(12) United States Patent
Camino

(10) Patent No.: US 6,656,187 B1
(45) Date of Patent: Dec. 2, 2003

(54) ADJUSTABLE ORTHOPAEDIC INSTRUMENT

(75) Inventor: Thomas Scott Camino, Warsaw, IN (US)

(73) Assignee: Depuy Products, Inc., Warsaw, IN (US)

( * ) Notice: Subject to any disclaimer, the term of this patent is extended or adjusted under 35 U.S.C. 154(b) by 0 days.

(21) Appl. No.: 10/233,703

(22) Filed: Sep. 3, 2002

(51) Int. Cl.⁷ .............................................. A61B 17/58
(52) U.S. Cl. ........................................ 606/85; 606/79
(58) Field of Search ............................ 606/79, 80, 82, 606/83, 84, 85

(56) References Cited

U.S. PATENT DOCUMENTS

| | | | |
|---|---|---|---|
| 4,738,681 A | | 4/1988 | Koeneman et al. |
| 4,739,750 A | | 4/1988 | Masse et al. |
| 4,756,711 A | * | 7/1988 | Mai et al. ................. 623/23.26 |
| 4,895,573 A | | 1/1990 | Koeneman et al. |
| 4,944,759 A | * | 7/1990 | Mallory et al. ........... 623/22.31 |
| 4,944,761 A | * | 7/1990 | Stuhmer et al. .......... 623/23.31 |
| 5,041,118 A | | 8/1991 | Wasilewski |
| 5,258,035 A | * | 11/1993 | Hofmann et al. ........ 623/23.28 |
| 5,360,446 A | | 11/1994 | Kennedy |
| 5,441,501 A | * | 8/1995 | Kenyon ....................... 606/85 |
| 5,507,829 A | * | 4/1996 | Thongpreda et al. .... 623/22.41 |
| 5,554,191 A | * | 9/1996 | Lahille et al. ........... 623/17.11 |
| 5,601,558 A | * | 2/1997 | Torrie et al. .................. 606/72 |
| 5,665,091 A | | 9/1997 | Noble et al. |
| 5,746,771 A | | 5/1998 | Clement, Jr. et al. |
| 5,993,455 A | | 11/1999 | Noble |
| 6,126,694 A | | 10/2000 | Gray, Jr. |

* cited by examiner

*Primary Examiner*—Pedro Philogene
*Assistant Examiner*—David A Bonderer

(57) ABSTRACT

A tool (10) for preparation of a cavity (12) in a long bone (14) for receiving a joint prosthesis (16) for use in arthroplasty is provided. The tool (10) includes a body (20) having an outer periphery (22) of the body (20). The outer periphery (22) is adapted to have a first shape (24) and a second shape (26) thereof of the body (20). The second shape (26) has dimensions different than the first shape (24), whereby the tool (10), when in the first shape (24), is capable of forming a first cavity (30) in the long bone (14) and whereby the tool (10), when in the second shape (26), is capable of forming a second cavity (32) in the long bone (14). The second cavity (32) is different than the first cavity (30).

19 Claims, 11 Drawing Sheets

ADJUSTABLE ORTHOPAEDIC
INSTRUMENT

TECHNICAL FIELD OF THE INVENTION

The present invention relates generally to the field of orthopaedics, and more particularly, to an implant for use in arthroplasty

BACKGROUND OF THE INVENTION

The invention relates to implantable articles and methods for manufacturing such articles. More importantly, the invention relates to bone prosthesis, bone prosthesis instrumentation and processes for manufacturing the same.

There are known to exists many designs for and methods for manufacturing implantable articles, such as bone prosthesis. Such bone prosthesis includes components for artificial joints, such as elbows, hips, knees and shoulders. An important consideration in the designing or manufacturing of any implantable bone prosthesis is that the prosthesis has adequate fixation when implanted within the body.

Earlier designs of implantable articles relied upon the use of cements, such as polymethylmethacrylate (PMMA) to anchor the implant. The use of such cements can have some advantages, such as providing a fixation that does not develop free play or does not lead to erosion of bone faces post-operatively. However, the current trend is to use these cements to a lesser extent because of their tendency to lose adhesive properties over time and the possibility that the cement contributes to wear debris within the joint. When utilizing these cement implants, the implants are designed to be smaller than the respective cavity. The implant is placed in the cavity and a mantel or layer of cement is applied between the cavity and the implant.

Recently, implantable bone prosthesis have been applied and designed such that they encourage growth of hard tissue (ie. bone) around the implant. The bone attachment usually occurs and growth is promoted when the surface of the implantable bone prosthesis is irregular or textured. The bone attachment usually occurs and growth is promoted when the surface of the implantable bone prosthesis has been found to provide a good fixation of the prosthesis with the body. A greater degree of bone fixation interaction of newly formed hard tissue in and around the texture can usually be achieved when bone-engaging surfaces of an implantable bone prosthesis are more porous or regular. For prostheses designed to encourage bone in-growth, the cavity into which the prosthesis is implanted closely conforms to the periphery of the bone prosthesis. Such bone prostheses are press-fitted into the bone cavity.

One of the considerations as to whether to use a cemented stem or a pressed-fitted stem in a prosthetic joint implant is the overall health or condition of the patient's bone. Long bones, particularly the femur, are typically classified into three general classifications of bone structure. These classifications are related to the health of the bone. The health of the bone is typically attributable to the progression of disease within the long bone. The typical long bone diseases that lead to total hip arthroplasty are ostoarthritis, avascular necrosis, and rheumatoid arthritis.

The three distinct classifications of bone structure of the femur can be identified between the metaphysis and the diaphysis. These three types of bone structures are type A, type B, and type C bone structure. These types of bone structure are more fully described in an article by Dorr, L D., Faugere, M C., Mackel, A M., Gruen, T A., Bogner, B., Malluche, H H. "Structural and Cellular Assessment of Bone Quality of Proximal Femur." *Bone* 1993: 231–242 hereby incorporated by reference in its entireties.

In Type A bone structures thick medial and posterior cortices are evident. They begin at the distal end of the lesser trochanter and are quite thick immediately. This creates both a narrow diaphyseal canal and a funnel shape to the proximal femur. The thicker cortices and less porosity result in a lower canal to calcar isthmus ratio. This type of bone is found more often in younger patients.

In Type B bone structures both the medial and posterior cortices exhibit bone loss. The medial cortex is thinned compared to Type A bone but a funnel shape is still present. The funnel shape of the canal remains good for implant fixation. The posterior cortex is especially thinned, or absent, and causes the width of the intramedullary canal to increase. The shape of the bone is proportional at the top and bottom.

In Type C bone structures the bone has lost nearly all the medial and posterior cortices, which result in a "stovepipe" shape of the intramedullary canal. It has the thinnest cortices of the 3 types of bone, a wide intramedullary canal, and appears somewhat "fuzzy" in x-rays. This type of bone is seen most often in older patients.

Cemented implants are more often used in patients with the type C bone structure, while cementless implants are more commonly used in patients with type A bone structure. Further, in many cases cemented implants are used in cases where the ratio where the proximal canal width to the distal canal width is less than the ratio for cases in which the cementless implants might be used.

Stem components for total joint arthroplasty typically have a wedge shape with the distal portion of the stem being smaller in cross section than the proximal cross section. Typically, the stem has a continually decreasing cross-sectional area in the direction from the proximal portion to the distal portion of the stem.

Due to the differences in the types of bone for which the cemented and cementless stems are designed, the shapes of the stems vary widely from one type of prosthetic stem to another. As mentioned before, some cemented stems have a larger difference between the cross-sectional area or width of the proximal portion of the stem to the distal portion of the stem.

Cemented and uncemented stems are implanted into a canal or cavity prepared in a resected long bone. The cavity in the long bone may be prepared utilizing at least one of several types of instruments. For example, the cavity may be prepared by a drill, reamer, or broach. A hip stem cavity may typically be prepared by a combination of drilling, reaming, and broaching. The broaching includes teeth or cutting edges which remove material from the bone. The broach generally has a shape equal to the shape of the stem.

In order to prepare a cavity for a particular stem, a unique broach with a unique profile must be available for preparing that cavity. Even for a particular stem, the surgeon may have patient-specific reasons or general-practice preferences for a cement mantel or thickness of the cement along the profile of the stem which may be different than that provided by the manufacturer of the stem and accompanying broaches. Thus, the prior art requires a vast number of broaches, namely, one for each particular size of a particular design of stem. And even with such a variety of stems, the configuration of a broach limits the surgeon to one particular cement mantel pattern for a particular hip stem and hip stem broach combination.

SUMMARY OF THE INVENTION

According to the present invention, an orthopedic implant tool includes a feature which permits a portion of the periphery of the instrument to be adjustable so that the tool may prepare more than one type of cavity for an orthopedic implant stem. The tool could be expanded or contracted to accommodate either a type A or a type C bone structure. Preferably, the expansion or contraction of the instrument is done in a controlled fashion such that a plurality of different feature sizes could be accommodated by one particular instrument.

The adjustable instrument permits the ideal sizing of the cavity for a particular implant. The adjustable instrument is able to replace separate instrument sets for cemented and cementless implants and reduces both cost and complexity for the manufacturer and the consumer of the instruments.

The present invention allows the same instrument or broach to create an envelope more conducive to the anatomical femur shape via either type A, type B, or type C bone structure and allows the implant to be ideally designed accordingly.

The adjustable instrument may be used for the reconstruction of any joint in which the intermedullary space of the long bone is prepared for a prosthesis. For example, the adjustable instrument may be utilized for shoulders, elbows, hips, and knees, as well as wrists and ankles. The adjustable instrument allows for the optimally designed cemented and cementless implants to fit into the operable broach envelope created by a single set of broaches.

According to one embodiment of the present invention, a tool for preparation of a cavity in a long bone for receiving a joint prosthesis for use in arthroplasty is provided. The tool includes a body having an outer periphery of the body. The outer periphery is adapted to have a first shape and a second shape of the body. The second shape has dimensions different than the first shape. The tool, when in the first shape, is capable of forming a first cavity in the long bone; and the tool, when in the second shape, is capable of forming a second cavity in the long bone. The second cavity is different than the first cavity.

According to another embodiment of the present invention, a hip joint prosthesis for cooperation with a long bone for use in arthroplasty is provided. A cavity is formed in the femur. The prosthesis includes a stem having portions of the stem for placement at least partially within the cavity of the femur. The stem defines a longitudinal axis of the stem. The prosthesis also includes a bearing for placement in the cavity between the stem and the femur so that the distal portion of the stem is spaced from the femur.

According to yet another embodiment of the present invention there is provided a broach for removal of bone for preparation of a cavity in a long bone for receiving a joint prosthesis for use in arthroplasty. The broach includes a body having an outer periphery of the body. At least portion of the body is capable of being flexed so that the outer periphery may have an expanded shape and a contracted shape of the body. The contracted shape has dimensions different than the expanded shape, whereby the tool when in the expanded shape is capable of forming a first cavity in the long bone; and the tool, when in the contracted shape, is capable of forming a second cavity in the long bone. The second cavity is different than the first cavity.

According to another embodiment of the present invention, an instrument kit for use in total joint arthroplasty is provided. The kit includes a broach for removal of bone for preparation of a cavity in a long bone for receiving a joint prosthesis. The broach includes a body having an outer periphery of the body. At least a portion of the body is capable of being flexed so that the outer periphery may have an expanded shape and a contracted shape of the body. The contracted shape has dimensions different than the expanded shape. The broach, when in the expanded shape, is capable of forming a first cavity in the long bone; and the broach, when in the contracted shape, is capable of forming a second cavity in the long bone. The second cavity is different than the first cavity.

According to a further embodiment of the present invention, a method for performing total joint arthroplasty comprising the steps of determining the appropriate implant stem to implant into the long bone, determining the appropriate size of cavity to prepare in the long bone, based on the size of the appropriate implant stem to implant, providing a broach having cutting path size adjustment capabilities, adjusting the cutting path size of the broach based on the appropriate size of cavity to prepare in the long bone, preparing a cavity in the medullary canal of a long bone with the broach, and installing the stem in the cavity of the long bone is provided.

The technical advantages of the present invention include the ability to customarily adjust the shape of the cavity for a prosthetic stem. For example, according to one aspect of the present invention, an instrument in the form of a broach includes a portion thereof which is expandable or contractible so that a portion of the broach may be enlarged or reduced to change the shape of the broach. Thus, the present invention provides for an adjustable customized cavity for a prosthetic stem.

Another technical advantage of the present invention includes the ability to replace a series of fixed broaches with a single adjustable broach. For example, according to one aspect of the present invention, the broach includes an adjustment feature such that the broach may be set in one of a series of different dimensions, each dimension corresponding to one a set of otherwise fixed broaches so that the adjustable broach can replace a plurality of fixed broaches. Thereby, the present invention replaces a series of broaches with a single broach.

Other technical advantages of the present invention will be readily apparent to one skilled in the art from the following figures, descriptions and claims.

BRIEF DESCRIPTION OF THE DRAWINGS

For a more complete understanding of the present invention and the advantages thereof, reference is now made to the following description taken in connection with the accompanying drawings, in which.

DETAILED DESCRIPTION OF THE INVENTION

Embodiments of the present invention and the advantages thereof are best understood by referring to the following descriptions and drawings, wherein like numerals are used for like and corresponding parts of the drawings.

Figure 1:
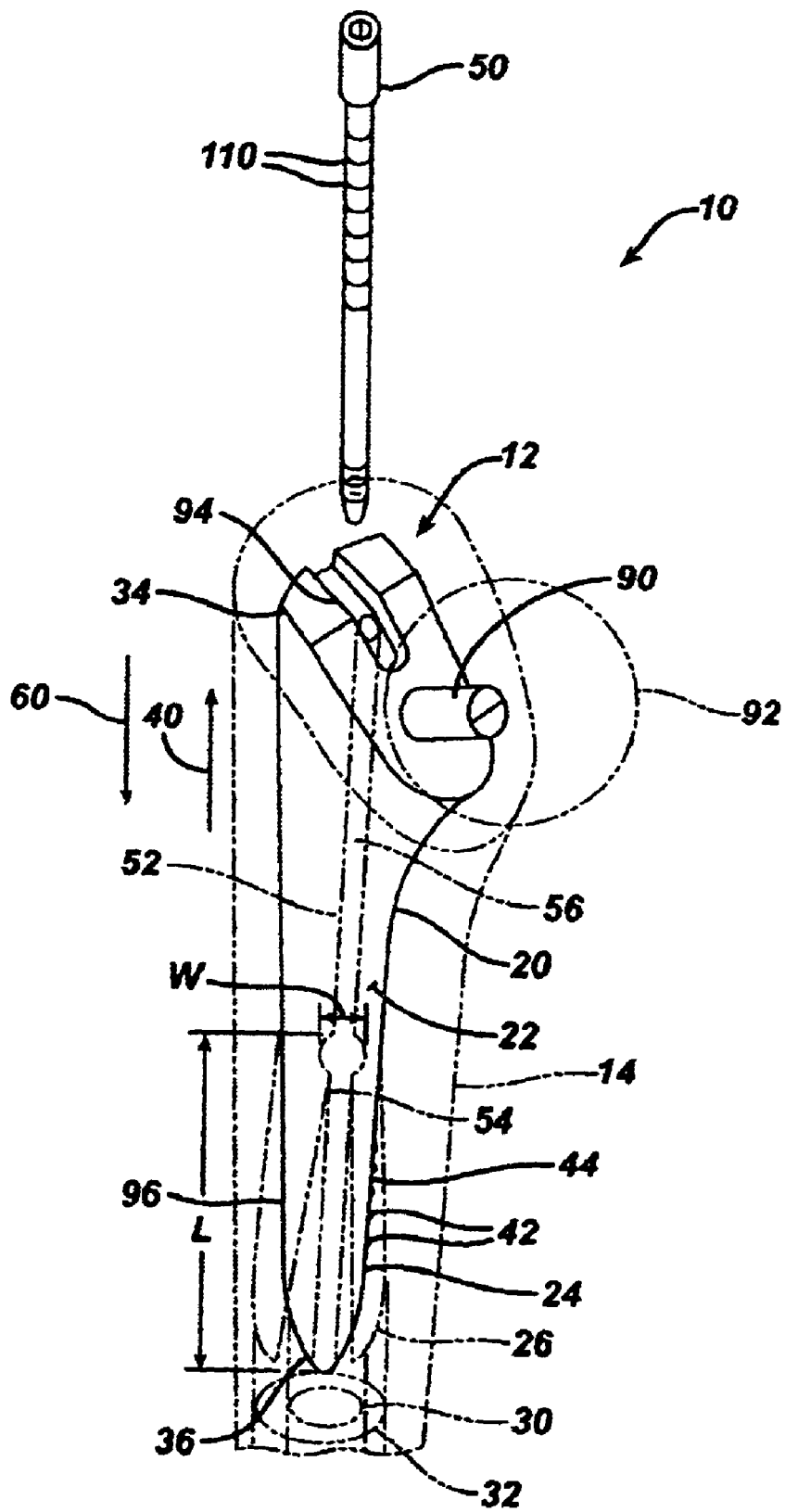
FIG. 1 is an exploded perspective view of an adjustable broach for preparing a cavity for a hip total joint prosthesis in accordance with an embodiment of the present invention.

According to the present invention referring now to FIG. 1, a tool 10 is shown. The tool is utilized for preparation of a bone cavity 12 in a long bone 14. The bone cavity 12 is utilized for receiving a joint prosthesis 16 (see FIG. 10) for use in arthroplasty. The tool 10 includes a body 20 having an outer periphery 22 of the body 20. The outer periphery 22 is adapted to have a first shape 24 and a second shape 26 of the outer periphery 22. The second shape 26 has dimensions different from those of the first shape 26.

The tool 10, when in the first shape 24, is capable of forming a first cavity 30 in the long bone 14. The tool 10, when in the second shape 26, is capable of forming a second cavity 32 in the long bone 14. The second cavity 32 is different than the first cavity 30.

The tool 10 may be made of any suitable durable material which is compatible with the human body and which may be of sufficient strength and hardness to remove bone from the bone cavity 12. For example, the tool 12 may be made of a metal, for example titanium, cobalt-chrome alloy steel, or stainless steel.

The tool 10 may have any suitable shape capable of repairing the bone cavity 12. Preferably, and as shown in FIG. 1, the tool 10 has a generally wedge shape or tapered shape having a wider proximal first end 34 and a narrower distal end 36. To provide for a shape of the cavity 12, which is compatible with an implant, the tool 10 may, for example, have a cross sectional shape which increases from the distal end 36 to the end proximal 34 in the direction of arrow 40.

The tool 10 may include features 42 on the outer periphery 22 of the tool 10 for assisting in the removal of bone from the long bone 14 to form the bone cavity 12. The features 42 may be in the form of, for example, cutting edges or teeth protruding from the outer periphery 22. These teeth 42 may be located anywhere along outer periphery 22 and may, for example, be located nearer the distal end 36 of the tool 10.

As shown in FIG. 1, the outer periphery 22 of the tool 10 may include a first cutting surface 44 which may, as shown in FIG. 1, be located toward the distal end 36 of the tool 10.

The tool 10 may also include a second cutting surface 46 opposed to the first cutting surface 44. The first cutting surface 44 and the second cutting surface 46 combine to shape the distal portion of the bone cavity 12.

It should be appreciated that according to the present invention, the tool 10 may be adapted to provide for both the first shape 24 and the second shape 26 of the tool 10 in any suitable manner. For example, the alteration of the tool 10 from the first shape 24 to the second shape 26 may be provided by having the tool 10 in the form of, for example, a collet or a diaphragm.

One particular suitable way of providing for a tool 10 having a first shape 24 and second shape 26 is providing the tool 10 in the form of a collet. In such a configuration as shown in FIG. 1, the body 20 is in the form of a collet and an actuator 50 is utilized to expand and retract the collet or body 20.

As shown in FIG. 1, the body may include a tool cavity 52 formed in the body 20. The actuator 50 in the form of, for example, a wedge is fittable partially within the tool cavity 52. The wedge or actuator 50 is adaptable to expand to at least a portion of the body 20 when the wedge 50 is fitted into the tool cavity 52.

The material from which the tool 10 is made, may be resilient to efficiently expand from a first shape 24 to a second shape 26. As shown in FIG. 1, to accommodate a less flexible and resilient material, the body may include a longitudinal slot 54 which assists in providing sufficient flexibility to the body 20. The slot 54 helps permit the second shape 26 to be substantially different from the first shape 24.

The longitudinal opening 54 may have any suitable shape; for simplicity, the longitudinal opening 54 may be in the form of a slot having a length L and a width W. The longitudinal slot 54 may, for simplicity, and to maximize the flexibility of the body 20, be centrally located about longitudinal axis 56 of the body 20.

The longitudinal slot 54 is preferably positioned adjacent one of the first cutting surface 54 and the second cutting surface 46. To maximize the flexibility of the body 20, the longitudal slot 54 may extend from distal end 36 of the body 20 in the direction of arrow 40 toward the proximal end 34 of the body 20. The distance L and width W, defining the dimensions of the longitudinal slot 54, may be selected to provide the optimum flexibility and strength of the tool 10.

It should be appreciated that the actuator 50 and the body 20 may cooperate with each other in any suitable fashion capable of providing the tool 10 with the first shape 24 and the second shape 26. For example, the actuator 50 may be utilized to expand the body or to retract the body. Further, the actuator may expand the body as it moves toward the body or may extend the body as it is separated from the body 20. The actuator may be located internally through the body 20 or may be positioned on the outer periphery of the body 20. The present invention may be practiced with a flexible or pliable body 20 and an actuator capable of moving or distorting the body from a first shape to a second shape.

Figures 2, 2A, 2B:
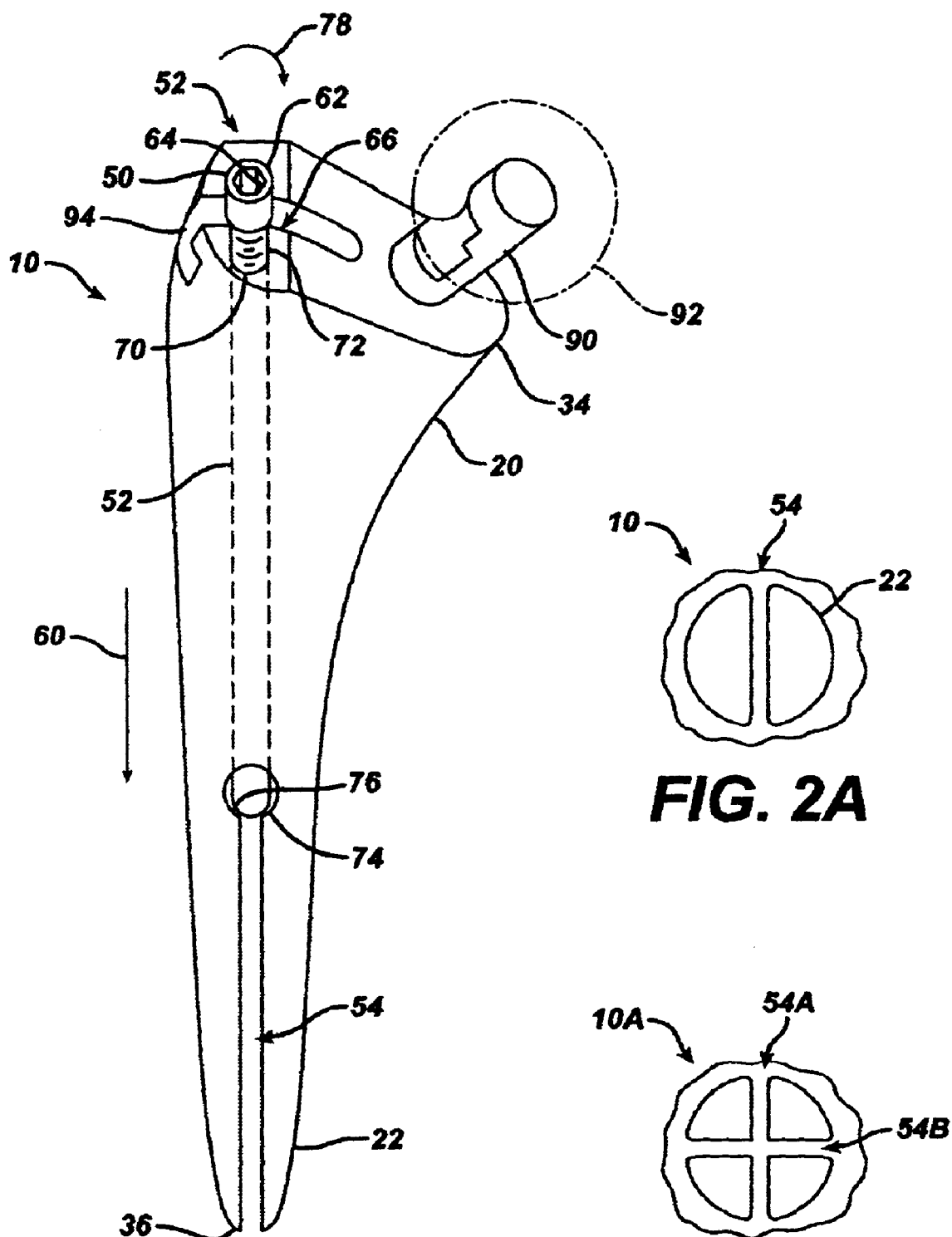
FIG. 2 is a perspective view of the adjustable broach of FIG. 1.
FIG. 2A is a portion bottom view of the adjustable broach of FIG. 1.
FIG. 2B is a portion bottom view of an adjustable broach similar to that of FIG. 1 having two perpendicular longitudinal slots in accordance to another embodiment of the present invention.
Figure 6:
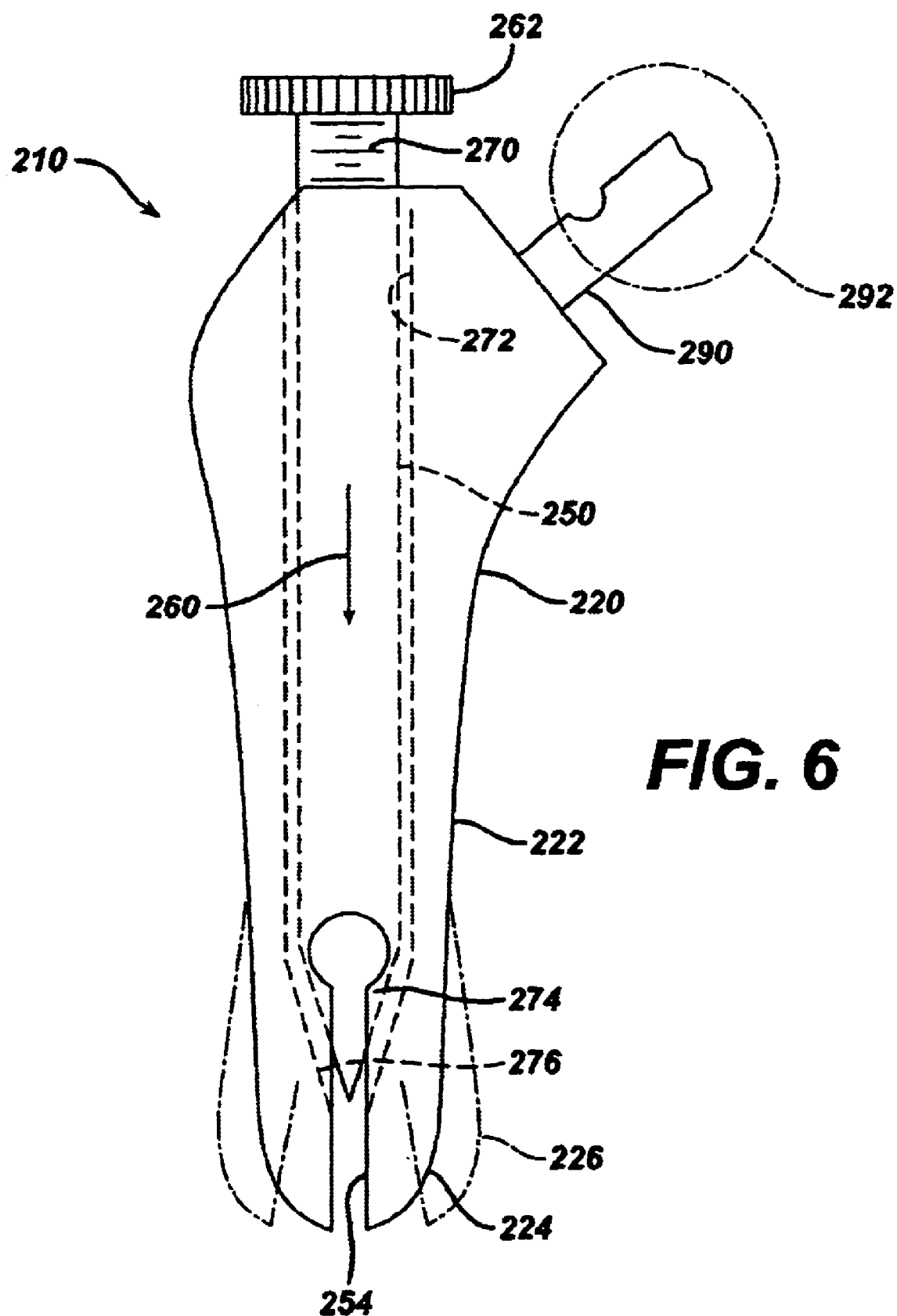
FIG. 6 is a plan view of an adjustable broach for preparing a cavity for a hip total joint prosthesis in accordance with another embodiment of the present invention.

One configuration of utilizing the body and actuator to provide a tool with a first shape and a second shape is shown as tool 10 in FIGS. 1, 2, 2A, and 3. Referring now to FIG. 2, the tool 10 is shown in greater detail. As shown in FIG. 2, the element 50 is in the form of a pin having a head 62 including a connector 64 in the form of interior slots. The interior slots as shown in FIG. 6 are shown in the form of a hexagonal internal socket.

The element 50 also includes a threaded portion 66 which has external threads 70 which cooperate with internal threads 72 on the body 20. As the element 50 is rotated by connector 64 utilizing a tool (not shown) in the direction of arrow 78, the element 50 is moved in the direction of arrow 60 toward distal end 36 of the body 20. As the element 50 moves in the direction of arrow 60, distal end 74 of the element 50 engages internal face 76 of the body 70 adjacent the longitudinal slot 54. As the end 74 of the element 50 continues to engage against the internal surface 76 of the body 20, the distal end 36 of the outer periphery 22 of the body 20 is caused to expand.

Referring now to FIG. 2B, an alternate embodiment of the present invention is shown as tool 10A. Tool 10A is similar to tool 10 of FIG. 1 except tool 10A has both a first longitudinal slot 54A and a second longitudinal slot 54B which is perpendicular to slot 54A.

Figure 3:
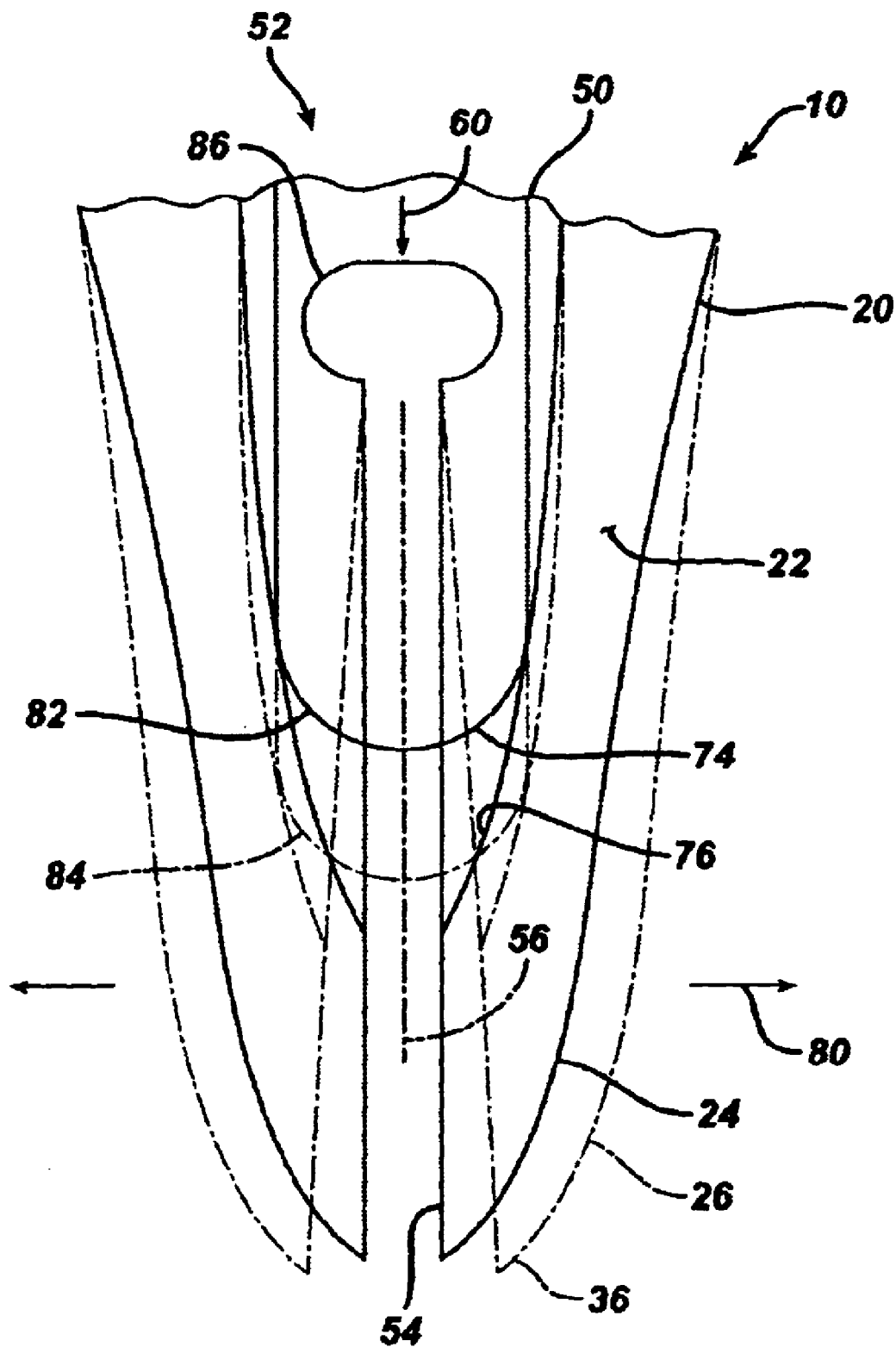
FIG. 3 is a partial plan view of the adjustable broach of FIG. 1.

Referring now to FIG. 3, the distal end 36 of the body 20 of the tool 10 is shown in greater detail. As the actuator element or rod 50 advances in the direction of arrow 60, eventually the rod 50 contacts the internal body surface 76 of the body 20 at distal end 74 of the rod 50. As the rod 50 continues to advance in the direction of arrow 60, the distal end 36 of the body 20 expands outwardly in the direction of arrows 80 such that when the rod 50 moves from first rod position 82 to second rod position 84, as shown in phantom, the outer periphery 22 of the body 20 at the distal end 36 of the body 20 moves from first shape 24 to second shape 26 as shown in phantom.

The rod end 74 may add any suitable shape, and as shown in FIG. 3, may have an arcular shape to avoid impingement of the rod end 74 against the internal body surface. As shown in FIG. 3, the rod end 74 is generally hemispherical. Any other suitable shape including any somewhat arcuate shape, for example, a generally conical shape may be satisfactory for the rod end 74. The internal body surface 76 may have any shape which generally provides for a internal body surface which moves inwardly toward longitudinal axis 56 when viewed in the direction of arrow 60 from the proximal end 34 to the distal end 36 of the body 20. As shown in FIG. 3, the internal body surface is generally conical in shape.

To improve the pliability and resiliency of the body 50, the body SO may include a relief 86 at the proximal end of the longitudinal slot 54. The relief 86 may have any shape, but as shown in FIG. 3, preferably has an arcuate shape which reduces stress concentration at the proximal end of the longitudinal slot 54.

Referring again to FIG. 2, the tool 20 may be utilized to assist in the trial reduction of an orthopedic implant. Thus, the tool can may be utilized, for example, as a trial stem. When utilized as a trial stem, the tool 10 may include neck 90 which extends outwardly from proximal end 34 of the body 20. The neck 90 is generally cylindrical and may have a tapered end (not shown).

A generally spherically trial head 92 may be positionable on the neck 90 and used to fit on either a acetabular cup or an acetabular cup trial. By utilizing the tool as a trial reduction, if the tool is not positioned deeply enough in the femur canal, the tool can be inserted more deeply into the canal and a further trial reduction performed.

Figure 4:
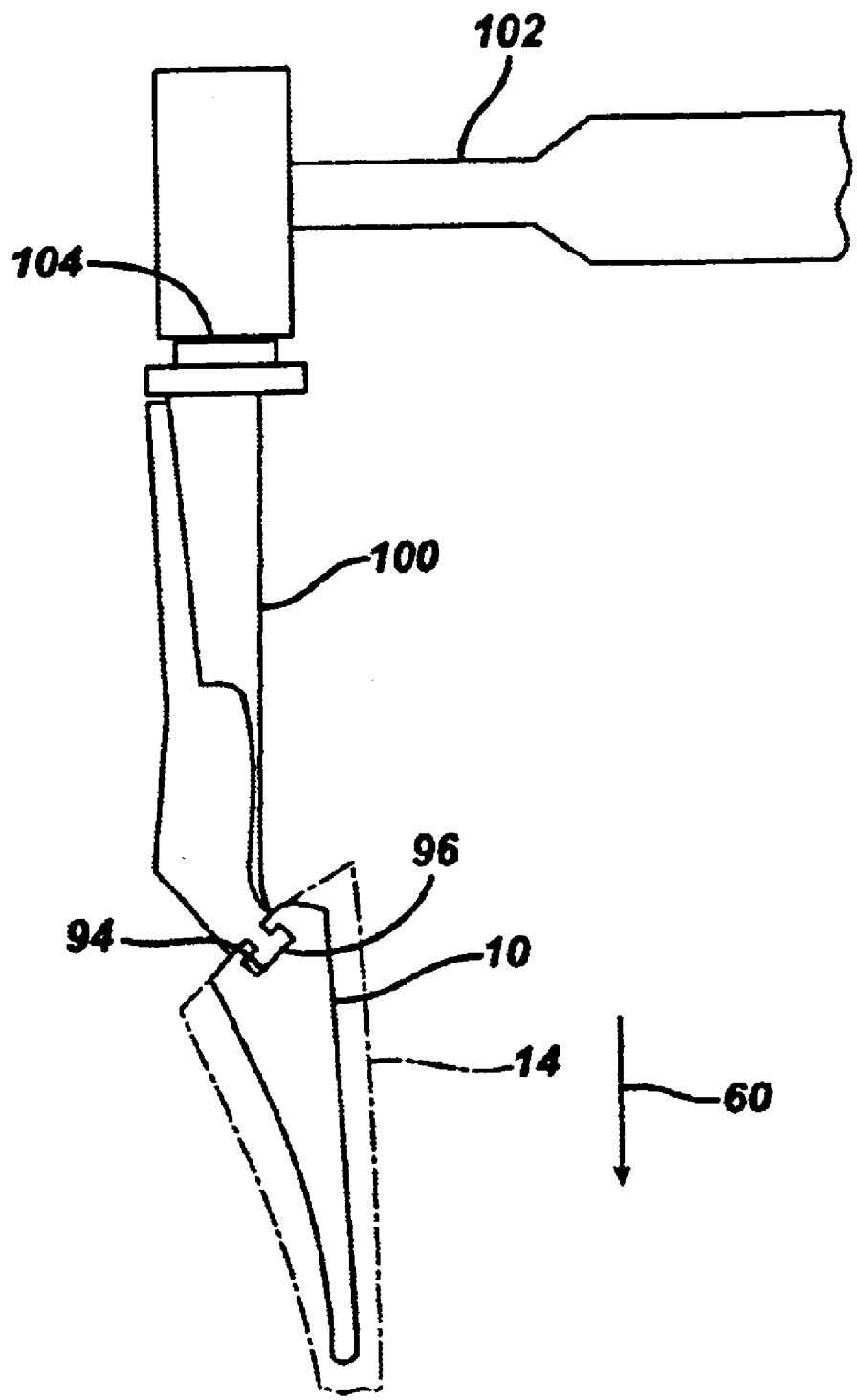
FIG. 4 is a partial plan view of a handle and hammer in use to position the broach of FIG. 1 in the cavity.

The tool 10 may be installed into the medullary canal of a long bone in any suitable fashion. For example, the tool 10 may be positioned in the canal by use of hand tools or power tools. For example, as shown in FIG. 1 and 4, the body 20 of the tool 10 may include a handle connection feature 94 in the form for example, a slot, which connects with a tool connection feature 96 on a broach handle 100. A mallot 102 is used to strike against upper end 104 of the handle 100 to advance the tool 10 in the direction of arrow 60.

Referring again to FIG. 1, while the invention can be practiced with a first shape 24 and a second shape 26 on the outer periphery 22 of the tool 10, it should be appreciated that the tool 10 may have the ability to provide for a wide variety of shapes depending on the position of the actuator 50. The tool 10 may thus include the ability to set or preset a particular position of the outer periphery 22 of the tool 10 so that a particular size of tool cavity may be provided.

For example, as is shown in FIG. 1, the actuator or rod 50 may include indicia 110 located along the length of the rod 50. The indicia 110 may be applied in any form. For example, the indicia 110 may be in the form of etched, printed, painted or cast marks that are positioned, for example, transverse to the longitudinal axis of the rod 50. The indicia 110 may also include numbers, letters, or other indicia to assist in determining a particular position along the rod 110.

The indicia 110, for example, may be used to position the rod such that a particular indicia 110 may be in line with proximal end 34 of the body 20. When utilizing the body 110, a particular marking from the indicia 110 may correspond to a particularly desired shape of the outer periphery 22 at the distal end 36 and a corresponding desired bone cavity size.

Figure 5:
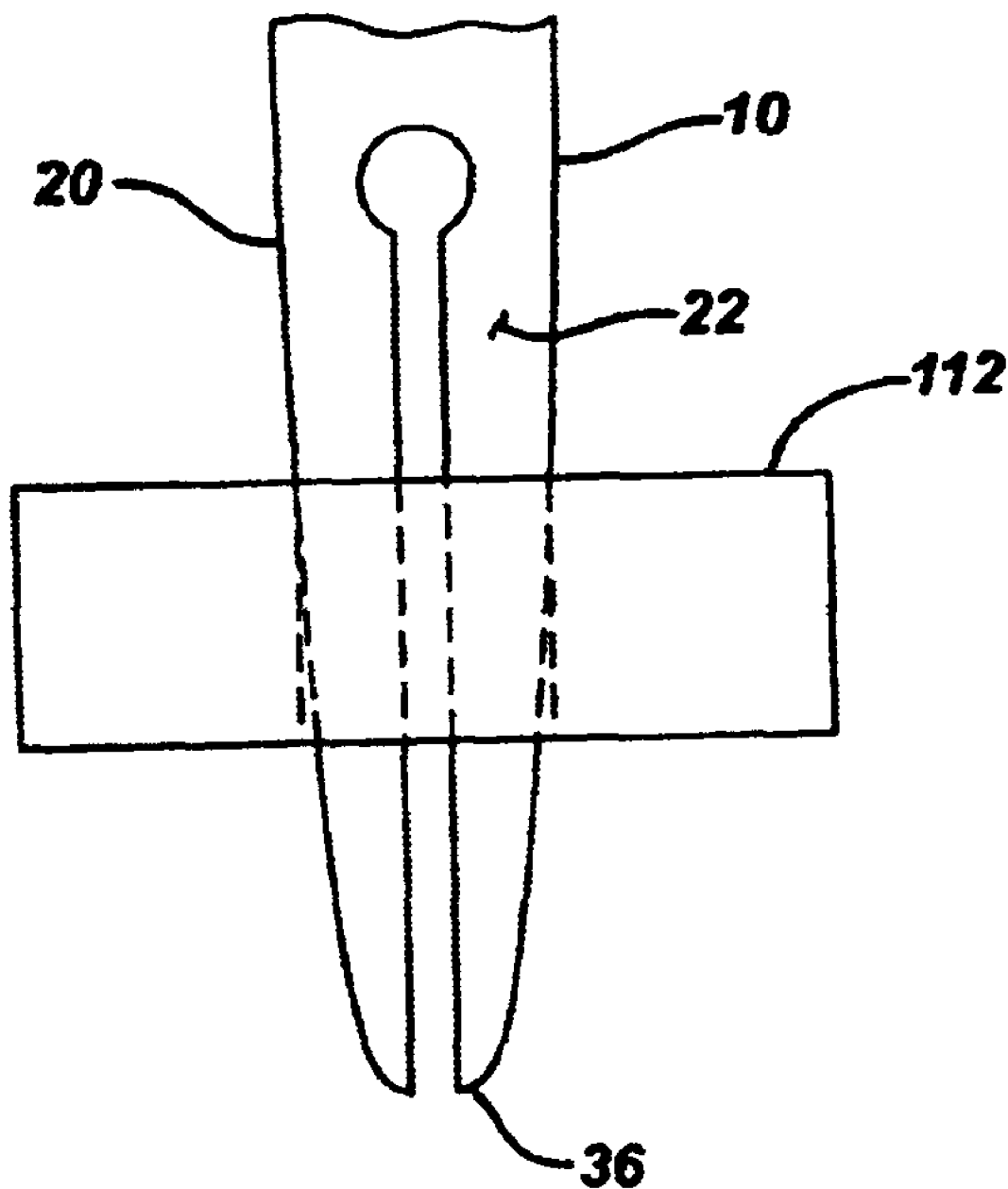
FIG. 5 is a plan view of a gage ring installed on the broach of FIG. 1.

Other methods for determining and presetting the shape of the outer periphery 22 of the tool 10 and the corresponding size of the bone cavity 12 may be provided. For example, referring now to FIG. 5, a device for presetting the tool 10 is in the form of a gage ring 112. A particular gage ring may slip over the distal end 36 of the outer periphery 22 of the body 20 of the tool 10. The gage ring 112 may correspond to a particular bone size cavity. It could be envisioned that one of a series of these rings may correspond to a particular size of the bone cavity.

Figure 7:
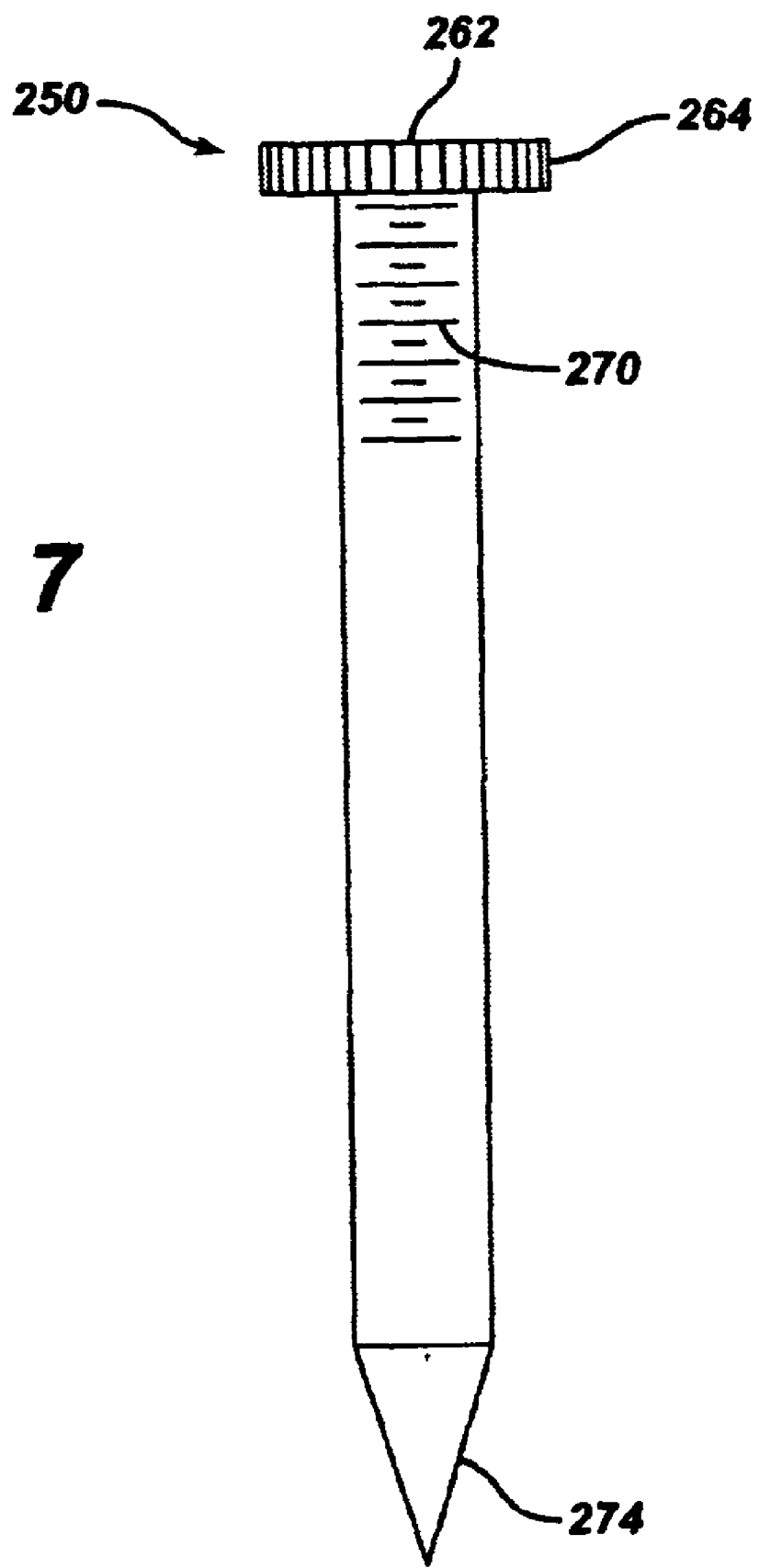
FIG. 7 is a plan view of an expander pin of the adjustable broach of FIG. 4.

Referring now to FIGS. 6 and 7, an alternative method to the present invention is shown as broach 210. The broach 210 includes a body 220 having a periphery 222. The body 220 is similar to body 20 of the broach 10 of the FIGS. 1 through 3 and may be made of a similar durable material, for example, a cobalt-chrome alloy steel, titanium, or a stainless steel. The body 220 may include a neck 290 onto which a trial head 292 may be fitted. The trial head 292 is similar to the trial head 92 of the broach 90 and is utilized to perform trial reductions.

The broach 210 may further include a rod 250 similar to the rod 50 of the broach 10 of FIGS. 1 through 3. Similarly to the rod 50 of the broach 10 of FIGS. 1 through 3, the rod 250 includes external threads 270 which mate with internal thread 272 on the body 220. The rod 250 includes a distal end 274 which contacts internal body surface 276 of the body 220. As the rod 250 moves in the direction of arrow 260, the rod 250 urges the outer periphery 222 of the body 220 from first shape 224 to second shape 226. Preferably, as shown in FIG. 4, the body 220 includes a longitudinal slot 254 to increase the flexibility of the body 220.

Referring now to FIG. 7, the rod 250 is shown in greater detail. The rod 250 includes external threads 270 which mate with the internal threads 272 of the body 220. The rod 250 includes a head 262 which includes knurls 264 to assist in the rotation of the rod 250. The rod 250 may be made of any suitable durable material and may for example be made of a metal that is compatable with the human anatomy and may be sterilizable. For example, the rod 250 may be made of stainless steel, a cobalt-chrome alloy steel, or titanium.

Figure 8:
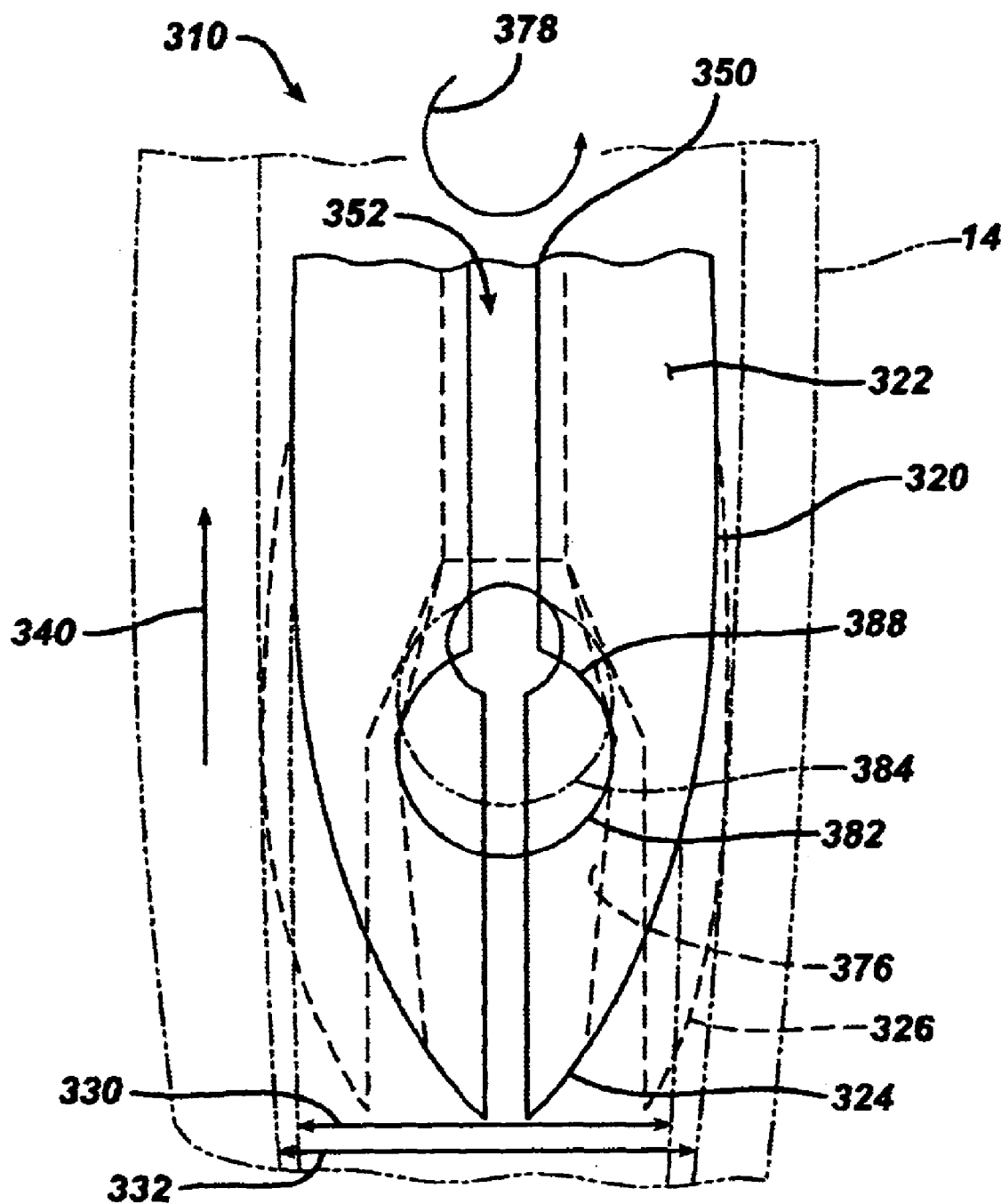
FIG. 8 is a partial plan view of an adjustable broach for preparing a cavity for a hip total joint prosthesis in accordance with a further embodiment of the present invention.

Referring now to FIG. 8, an alternative embodiment of the present invention may be shown as broach 310. Broach 310 is similar to broach 10 of FIGS. 1 through 3, except that broach 310, unlike broach 10 of FIGS. 1 through 3, has a protrusion 388 on the actuator 350 which causes outer periphery 322, of the broach 310 to expand when the rod 350 is operated in the direction of arrow 340. This direction of rod motion that causes the broach 310 to expand is opposite to that which causes the broach 10 to expand.

The broach 310 is preferably made of a similar material to that of broach 10. For example, the broach may be made of a metal in the form stainless steel, cobalt-chrome alloy steel, or titanium. Likewise, the actuator 350 may be made of a similar suitable durable material as the actuator 50 of the broach in FIGS. 1 through 3. The actuator 50 may be made of, for example, a stainless steel, titanium, or a cobalt chrome alloy steel.

The broach 310 includes the actuator 350 which is positioned in cavity 352 of the body 320 of the broach 310. As the actuator 350 is rotated in the direction of arrow 378, the actuator 350 is caused by threads (not shown) to move in the direction of arrow 340. As the actuator 350 moves in the direction of arrow 340, the protrusion 388 on the actuator 350 contacts internal body surface 376 of the body 320. Thus, as the rod moves from first rod position 382 to second rod position 384 in the direction of arrow 340, the outer periphery 322 of the body 320 of the broach 310 moves from first shape 324 to second shape 326. When the periphery 322 of the broach 310 is in first position 324, a first cavity 330 may be formed. Conversely, when periphery 322 of the broach 310 is in second position 326, second cavity 332 may be formed.

Figure 9:
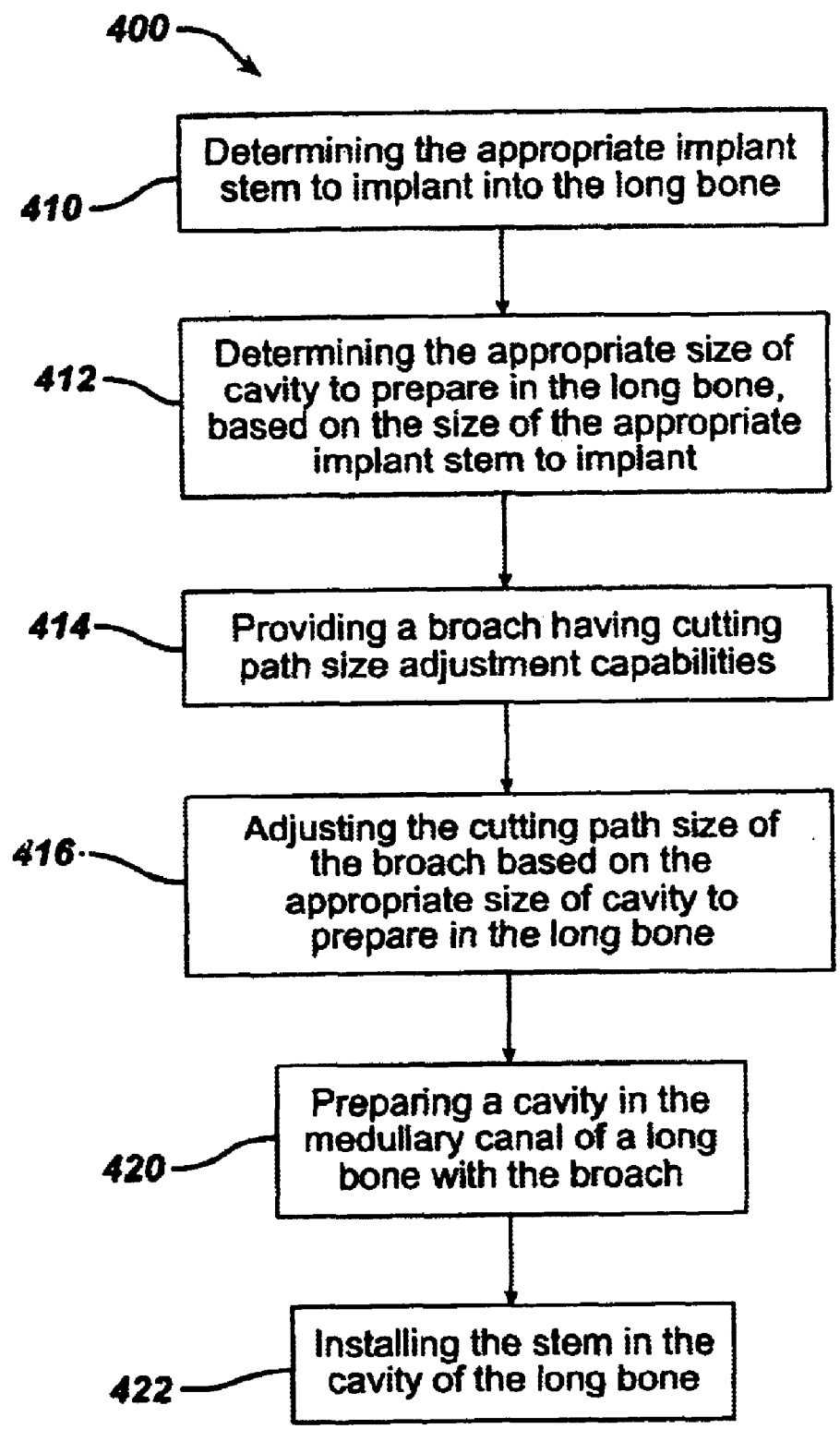
FIG. 9 is a process flow chart for a method of preparing a cavity for a hip total joint prosthesis according to a further embodiment of the present invention.

Referring now to FIG. 9, method 400 for performing joint arthroplasty is shown. The method 400 includes a first step 410 of determining the appropriate implant stem to implant into the long bone. The method 400 further includes a second step 412 of determining the appropriate size of the cavity to prepare in the long bone based on the size of the appropriate implant stem to implant. The method 400 further includes a third step 414 of providing a broach having cutting path size adjustment capabilities. The method 400 further includes a fourth step 416 of adjusting the cutting path size of the broach based on the appropriate size of cavity to prepare in the long bone. The method 400 further includes a fifth step 420 of preparing a cavity in the medullary canal of a long bone with the broach. The method 400 also includes a sixth step 422 of installing the stem in the cavity of the long bone.

Figure 10:
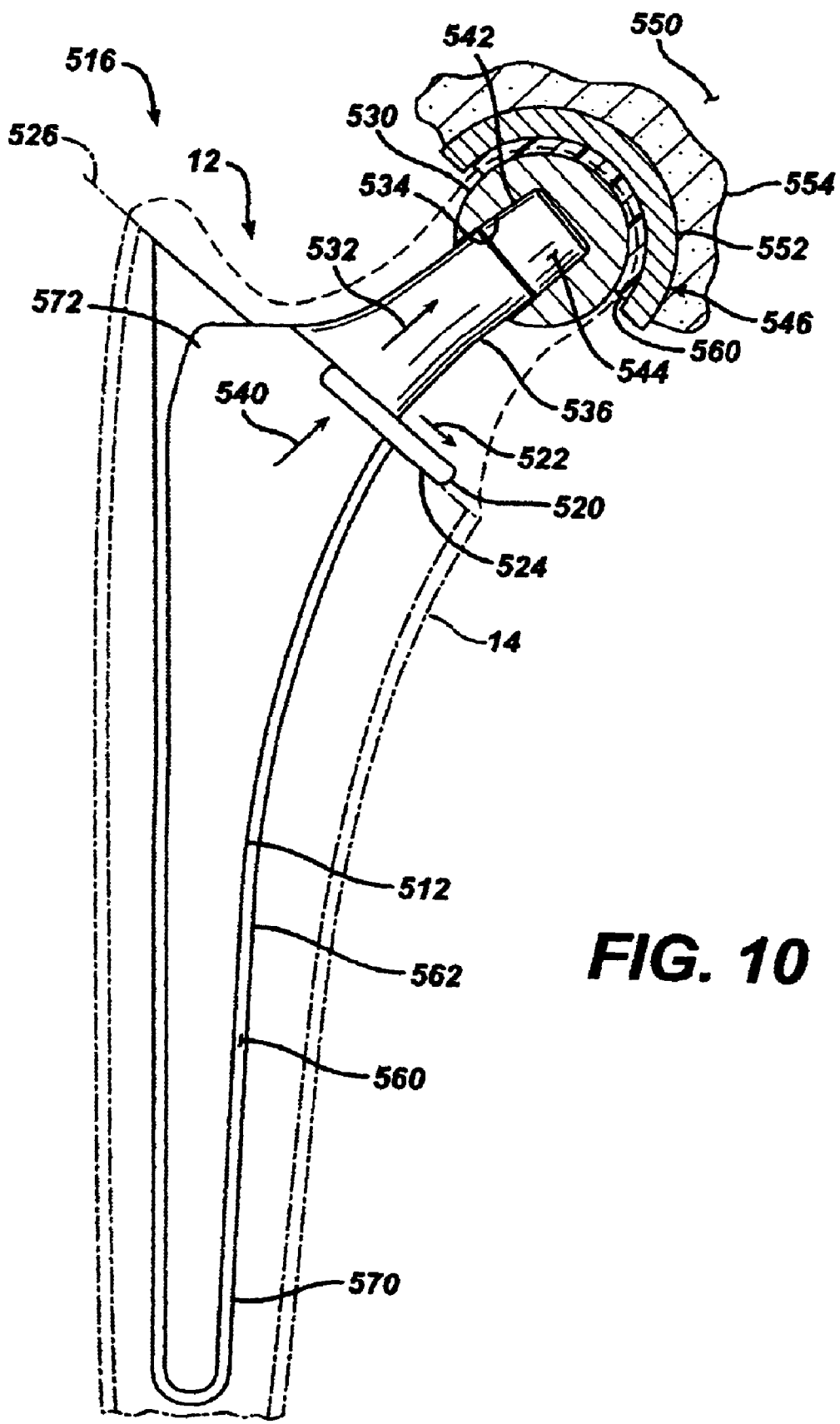
FIG. 10 is a plan view partially in cross section of a hip joint prosthesis which may utilize the cavity formed by the adjustable broach of the present invention.

Referring now to FIG. 10, a prosthesis 516 is shown which may be utilized in the bone cavity formed by the tool or broach of the present invention. The prosthesis 516 may be in the form of a hip prosthesis. The prosthesis 516 includes a stem 512.

As shown in FIG. 1, the stem 512 is suitable for implantation at least partially within bone canal 12 of the long bone 14. The prosthesis 516 includes a collar 520 for positioning the prosthesis 516 within the long bone 14 during surgery. The collar 520 is operably associated with the stem 512 and extends outwardly in the direction of arrow of 522 from the stem 512. As shown in FIG. 10, the collar 20 may include a collar face 524 which is positioned against the resected surface 526 of the long bone 14. The collar 520 thus serves to support the prosthesis 516 against the long bone 14 and to provide a reference for proper positioning of the prosthesis 516 within the bone canal 12 over long bone 14.

The prosthesis 516 may further include a head 530 which is operably associated with the stem 512. The head 530 may be operably associated with the stem in any suitable manner.

For example, the head 530 may include a cono-frustrical recess 532 forming an internal tapered surface 534.

As shown in FIG. 10, the stem 12 may include a neck 536 extending approximately in the direction of arrow 540 from the collar 520. The neck 536 may include an externally tapered portion 542 having externally tapered surface 544. As shown in FIG. 10, the external surface 544 of the tapered portion 542 of the neck 536 is matingly fitted to the internal surface 534 of the head 530.

The prosthesis 516 may further include a cup 546 for a pivotal engagement with head 530. The cup 546 may be secured to hip bone 550 in any suitable fashion. For example, the cup 546 may include a hemispherical outer surface 552 which fits to acetabulum 554 of the hip bone 550.

The outer surface 552 of the cup 546 may include openings (not shown) to which fasteners (not shown) are fitted for securement to the acetabulum 554 or may include a threaded periphery (not shown) for engagement with the acetabulum 554.

The cup 546 may be in pivotal engagement with the head 530 in any suitable fashion. For example, the head 530 and the cup 546 may have mating surfaces for metal to metal contact with each other or, as shown in FIG. 10 a liner 560 may be pivotally located between the cup 546 and the head 530. The liner 560 may be made of a durable metal or be made of a nonmetallic material, for example, a plastic or a ceramic.

For example, the liner 560 may be made of a high or ultra-high molecular weight polyethylene. For example, the liner 560 may be made of a ultra-high molecular weight polyethylene. One particular ultra-high molecular polyethylene that is well suited by this application is sold by DePuy as Marathon® and is generally described in U.S. Pat. No. 6,017,975 and 6,228,900 which are hereby incorporated by reference in their entireties.

Figure 11:
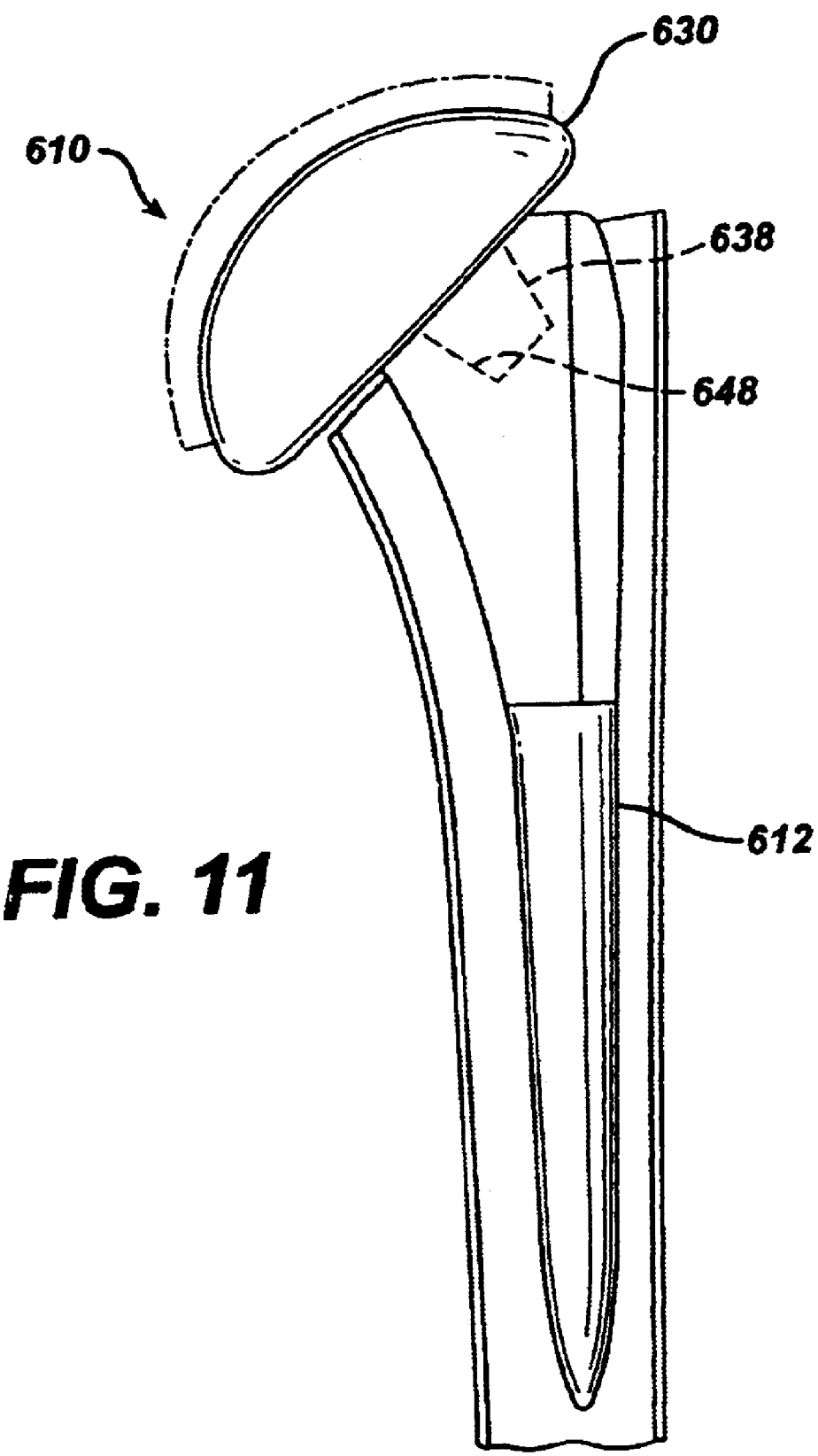
FIG. 11 is a plan view partially in cross section of a shoulder joint prosthesis which may utilize the cavity formed by the adjustable broach of the present invention.

Referring now to FIG. 11, a prosthesis which may be utilized with the broach of the present invention is shown in the form of a shoulder prosthesis 610. The shoulder prosthesis 610 includes a stem 612 for placement in the humeral cavity. The shoulder prosthesis 610 also includes a head 630 having a connection pin 638. The connection pin 638 in the head 630 interlocks with a tapered cavity 648 in the stem 612. The head 630 mates with a glenoid implant (no shown) which is positioned in the glenoid cavity.

The broach of the present invention can be adjusted into a plurality of peripheral dimensions which can be used to form multiple cavities in the medullarly canal with a solitary broach. The use of this multicavity-forming broach will provide for fewer instruments for simplicity, reduced handling, less weight of the instrument cases and trays, reduced loss and wear of instruments, and reduced inventory cost for the broach instruments.

Additionally, the creation of the instrument set with the adjustable broach will permit a surgeon to implant either cemented or cementless implants in their patients with varying anatomies with a common adjustable broach. This adjustable broach is ideal for surgical simplicity and a comprehensive implant system.

The adjustable broach of the present invention allows the same broach to create an envelope which is more conductive to the anatomical femur shape whether that be a type A, a type B, or a type C femur and allows the implant to be optionally designed for a particular femur bone condition.

It should be appreciated that the adjustable broach of the present invention could be used for the reconstruction of any joint in which the intermedullary space of a long bone is prepared for prosthesis. For example, the tool or broach of the present invention may be used for shoulder prosthesis, hip prosthesis, elbow prosthesis, or knee prosthesis.

Although the present invention and its advantages have been described in detail, it should be understood that various changes, substitutions, and alterations can be made therein without departing from the spirit and scope of the present invention as defined by the appended claims.

What is claimed is:

1. A tool for preparation of a cavity in a long bone for receiving a joint prosthesis for use in arthroplasty, said tool comprising a body having an outer periphery thereof, the outer periphery adapted to have a first shape and a second shape thereof, the second shape having dimensions different than the first shape, whereby said tool, when in the first shape is capable of forming a first cavity in the long bone and whereby said tool when in the second shape is capable of forming a second cavity in the long bone, the second cavity being different than the first cavity in the distal portion of the second cavity and substantially the same in the proximal portion of the second cavity.

2. A tool as in claim 1, wherein said body defines a first cutting surface thereof and a second cutting surface thereof, the first cutting surface and the second cutting surface being opposed to each other.

3. A tool as in claim 1:
   wherein said body defines a cavity therein; and
   further comprising a wedge fittable at least partially within the cavity, the wedge adaptable to expand at least a portion of said body when said wedge is fitted into the cavity.

4. A tool as in claim 1:
   wherein said body defines a longitudinal slot extending inwardly from one end of said body; and
   further comprising an element cooperable with said body to expand said body adjacent the slot.

5. A tool as in claim 4, wherein said body defines second longitudinal slot at least partially spaced from said first mentioned longitudinal slot.

6. A tool as in claim 1:
   wherein said body defines a longitudinal opening extending from one end of said body to the other end of said body; and
   further comprising an element cooperable with said body to expand said body adjacent the opening.

7. A tool as in claim 1:
   wherein said body defines a longitudinal opening extending from the proximal end of said body to the distal end of said body;
   wherein said body further defines a longitudinal slot formed therein and extending inwardly from the distal end of said body; and
   further comprising a rod fitable at least partially within the opening and cooperable with said body to expand said body adjacent the slot.

8. A tool as in claim 7:
   wherein said rod includes rod features; and
   wherein said body includes body features, the rod features being cooperable with the body features to expand said body adjacent the slot.

9. A tool as in claim 7, wherein said body and said rod are adapted to expand said body adjacent the slot as said rod is advanced distally relative to said body.

10. A tool as in claim 7, wherein said body and said rod are adapted to expand said body adjacent the slot as said rod is advanced proximately relative to said body.

11. A broach for removal of bone for preparation of a cavity in a long bone for receiving a joint prosthesis for use in arthroplasty, the broach comprising a body having an outer periphery thereof, at least portion of said body being capable of being flexed so that the outer periphery has an expanded shape and a contracted shape thereof, the contracted shape having dimensions different than the expanded shape, whereby the tool when in the expanded shape is capable of forming a first cavity in the long bone and whereby the tool when in the contracted shape is capable of forming a second cavity in the long bone, the second cavity being different than the first cavity.

12. A broach as in claim 11, wherein said body defines a first cutting surface thereof and a second cutting surface thereof, the first cutting surface and the second cutting surface being opposed to each other.

13. A broach as in claim 11:
   wherein said body defines a longitudinal slot extending inwardly from one end of said body; and
   further comprising an element cooperable with the slot or slots to at least one of expand and contract said body adjacent the slot.

14. A broach as in claim 11:
   wherein said body defines a longitudinal opening extending from one end of said body to the other end of said body; and
   further comprising an element cooperable with said body to at least one of expand and contract said body adjacent the opening.

15. A broach as in claim 11:
   wherein said body defines a longitudinal opening extending from the proximal end of said body to the distal end of said body;
   wherein said body further defines a longitudinal slot extending inwardly from the distal end of said body; and
   further comprising a rod fittable at least partially within the opening and co-operable with said body to one of expand and contract said body adjacent the slot.

16. A broach as in claim 15:
   wherein said rod includes rod features;
   wherein said body includes body features, said rod features being cooperable with the body features to one of expand and contract said body adjacent the slot.

17. A broach as in claim 15, wherein said body and said rod are adapted to one of expand and contract said body adjacent the slot as said rod is advanced one of proximally and distally relative to said body.

18. A broach as in claim 15, wherein at least one of said body and said rod include indicia thereon corresponding to the relative position of said body with respect to said rod.

19. An instrument kit for use in total joint arthroplasty the kit comprising a broach for removal of bone for preparation of a cavity in a long bone for receiving a joint prosthesis, said broach including a body having an outer periphery thereof, at least portion of said body being capable of being flexed so that the outer periphery has an expanded shape and a contracted shape thereof, the contracted shape having dimensions different than the expanded shape, whereby said broach when in the expanded shape is capable of forming a first cavity in the long bone and whereby said broach when in the contracted shape is capable of forming a second cavity in the long bone, the second cavity being different than the first cavity.

* * * * *